United States Patent
Jansen

(10) Patent No.: US 6,677,465 B2
(45) Date of Patent: Jan. 13, 2004

(54) METHOD FOR THE ENANTIOSELECTIVE PREPARATION OF 3,3-DIPHENYL-2,3-EPOXY PROPIONIC ACID ESTERS

(75) Inventor: Rolf Jansen, Mannheim (DE)

(73) Assignee: Abbott GmbH & Co. KG, Wiesbaden (DE)

(*) Notice: Subject to any disclaimer, the term of this patent is extended or adjusted under 35 U.S.C. 154(b) by 0 days.

(21) Appl. No.: 10/181,457

(22) PCT Filed: Jan. 12, 2001

(86) PCT No.: PCT/EP01/00322

§ 371 (c)(1),
(2), (4) Date: Oct. 29, 2002

(87) PCT Pub. No.: WO01/53281

PCT Pub. Date: Jul. 26, 2001

(65) Prior Publication Data

US 2003/0162982 A1 Aug. 28, 2003

(30) Foreign Application Priority Data

Jan. 20, 2000 (DE) .......................... 100 02 393

(51) Int. Cl.$^7$ ............................................. C07D 301/02
(52) U.S. Cl. ............................................ 549/518; 560/57
(58) Field of Search .................... 549/518; 560/57

(56) References Cited

FOREIGN PATENT DOCUMENTS

WO    96/11914    4/1996

OTHER PUBLICATIONS

Kagan, J. et al, 'Molecular rearrangements with ethoxycarbonyl group migrations. 2. Rearrangement of 1,2–glycols, halohydrins, and azidohydrins' CA 85:45791 (1976).*
Mukaiyama,T. et al 'Reductive cross–coupling reaction of a glyoxylate with carbonyl compounds. A facile synthesis of .alpha.,.beta.–dihydroxylate based on a low valent titanium compound' CA 112:138694 (1990).*
J.Org.Chem.1990,55,1957–1959, Denis et al.

* cited by examiner

*Primary Examiner*—Amelia Owens
(74) *Attorney, Agent, or Firm*—Wood, Phillips, Katz, Clark & Mortimer

(57) ABSTRACT

The invention relates to a process for the enantioselective preparation of glycide ester (I) by (a) dihydroxylation of a corresponding 3-phenyl cinnamate (II) by osmium (VIII) oxide catalysis in the presence of a Sharpless ligand and an oxidizing agent to form the dihydroxy ester (III),
(b) selective conversion of the hydroxy function in position 2 of the dihydroxy ester (III) to a leaving group,
(c) intramolecular substitution of the leaving group through the hydroxy function in position 3 to form the glycide ester (I),

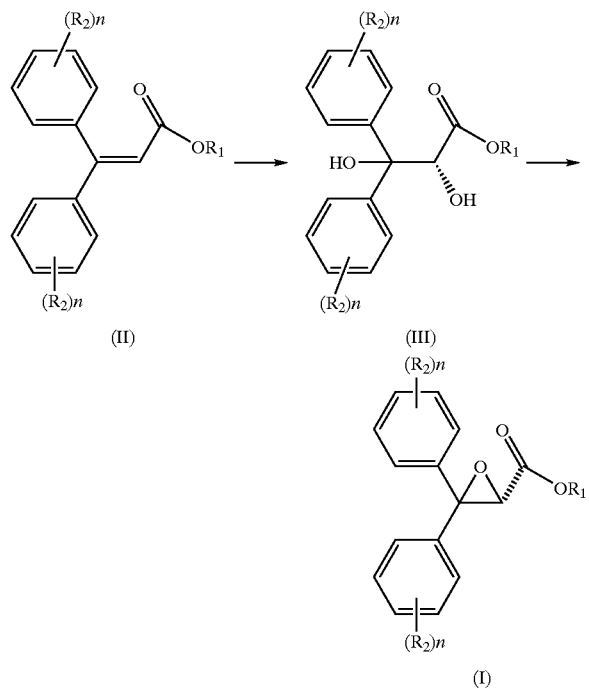

in which $R_1$ denotes $C_1$–$C_{10}$ alkyl, aryl, or arylalkyl, which may be substituted, $R_2$ denotes $C_1$–$C_{10}$ alkyl, aryl, arylalkyl, halogen, $C_1$–$C_{10}$ alkoxy, acyloxy, or amide, which may be substituted, and n is 0 to 5.

3 Claims, No Drawings

METHOD FOR THE ENANTIOSELECTIVE PREPARATION OF 3,3-DIPHENYL-2,3-EPOXY PROPIONIC ACID ESTERS

DESCRIPTION

The present invention relates to a process for the transformation of 3-phenyl cinnamate to enantiomerically pure 3,3-diphenyl-2,3-epoxy propionate.

3,3-Diphenyl-2,3-epoxy propionates are important intermediate products for the synthesis of biologically active substances, such as are described in, for example, Patent Applications WO 96/11914, WO 97/38981, DE 1963046.3 and DE 19944049.2. Said references describe the production of these active substances via racemic and enantiomerically pure glycide esters. In the racemic process the glycide ester is provided by Darzen's synthesis of glycide ester. The racemic process suffers from the drawback that in a subsequent stage the undesirable enantiomer must be separated, which gives rise to a loss in total yield.

In said process for the preparation of enantiomerically pure glycide esters, 3-phenyl cinnamates are used as starting materials, which are transformed by Jacobsen epoxidation. This variant has however the drawback that the enantiomeric purities attained are only ca 85% e.e. and clean-up of the products is very elaborate. Thus these known processes are only useful to a limited extent in manufacturing processes intended for use on an industrial scale.

It is thus an object of the present invention to provide a process to the production of 3,3-diphenyl-2,3-epoxy propionate, which guarantees high enantiomeric purity and can be used on an industrial scale.

We have found a process for the enantioselective production of glycide ester by (a) dihydroxylation of a corresponding 3-phenyl cinnamate (II) by osmium (VIII) oxide catalysis in the presence of a Sharpless ligand and an oxidizing agent to form the dihydroxy ester (III), (b) selective conversion of the hydroxy function in position 2 of the dihydroxy ester (III) to a leaving group, (c) intramolecular substitution of the leaving group through the hydroxy function in position 3 to produce the glycide ester (I),

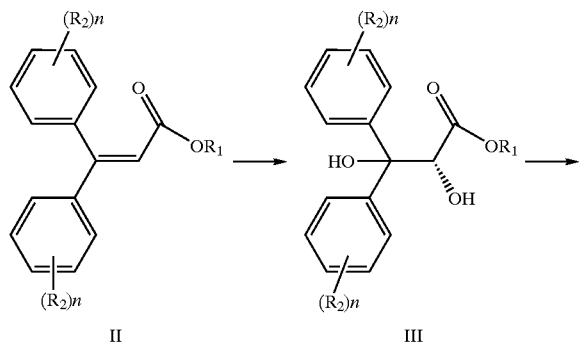

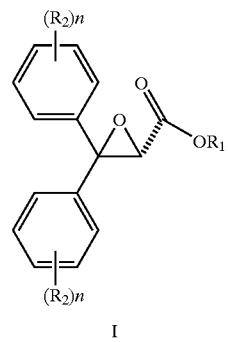

in which
R$_1$ denotes C$_1$–C$_{10}$ alkyl, aryl or arylalkyl, which may be substituted,
R$_2$ denotes C$_1$–C$_{10}$ alkyl, aryl, arylalkyl, halogen, C$_1$–C$_{10}$ alkoxy, hydroxy, acyloxy, amide, or amine, which may be substituted,
n is 0 to 5.

The reaction step (a) is an asymmetrical dihydroxylation such as has been described, for example, by Sharpless. Sharpless dihydroxylation and the use thereof have been described in detail by H. C. Kolb, M. S. Van Niewenhze, and K. B. Sharpless, in Chem. Rev. 1994, 94, 2483, the contents of which are included herein by reference. An article by L. Ahrgren and L. Sutin in Organic Process Research & Development 1997, 1, 425–427 has shown that the reaction should basically be executable on a greater scale (upscaleable).

By an osmium (VIII) oxide catalyst is meant an oxygen compound of osmium showing a level of oxidation of +VIII; OsO$_4$ and K$_2$OsO$_2$(OH)$_4$ are preferred.

The osmium (VIII) oxide need not be used in a stoichiometric amount relatively to the substrate of formula (II) but can, as catalyst, be employed in very much smaller quantities, the spent catalyst being regenerated by an oxidizing agent.

The osmium (VIII) oxide catalyst is usually used in amounts of from 0.1 to 5 mol % and preferably from 0.1 to 2.5 mol %, based on the substrate of formula (II).

By Sharpless ligands are meant compounds which are chiral, possess a nitrogen-containing six-membered heterocycle, bind to OsO$_4$, and accelerate OsO$_4$-dependent dihydroxylation.

Such Sharpless ligands are preferably hydroquinine and hydroquinidine derivatives as disclosed, for example, in the above literature. Preference is given to hydroquinine-(1,4-phthalazine-diyl diether) (DHQ)2PHAL or hydroquinidine-(1,4-phthalazine-diyl diether) (DHQD)2PHAL or hydroquinine-(2,5-diphenyl-4,6-pyrimidine-diyl diether) (DHQ)2PYR or hydroquinidine-(2,5-diphenyl-4,6-pyrimidine-diyl diether) (DHQD)2PYR.

The choice of Sharpless ligand is naturally governed by the desired enantiomer (III). Depending on the side from which the attack by (II) on the double bond to be hydroxylated is to take place, a corresponding Sharpless ligand must be selected according to the known mechanistic rules of Sharpless.

Suitable oxidizing agents for step (a) are those materials which are capable of reconverting the osmium oxide reduced during dihydroxylation of the double bond to its active level of oxidation of +VIII, ie materials which permit reactivation of the dihydroxylation catalyst. Such oxidizing agents can be readily found by considering their electrochemical potential. Well suited oxidizing agents are, for example, oxygen, hydrogen peroxide, N-methylmorpholine-N-oxide (NMO), potassium hexacyanoferrate, the AD-mix described by Sharpless (J. Org. Chem., 1992, 57, 2768), or alternatively electochemical processes.

Further oxidizing agents are described, for example, by M. Schröder, Chem. Rev. 1980, 80, 187–213.

The oxidizing agents used are preferably oxygen, hydrogen peroxide, N-methylmorpholine-N-oxide, potassium hexacyanoferrate, and electrochemical processes.

A particularly suitable mixture for use in an industrial reaction according to (a) has been found to be a mixture of from 0.1 to 1.5 mol % of $K_2OsO_2(OH)_4$, from 0.1 to 3 mol % of hydroquinine-(1,4-phthalazine-diyl diether) (DHQ) 2PHAL or hydroquinidine-(1,4-phthalazine-diyl diether) (DHQD)2PHAL or hydroquinine-(2,5-diphenyl-4,6-pyrimidine-diyl diether) (DHQ)2PYR or hydroquinidine-(2,5-diphenyl-4,6-pyrimidine-diyl diether) (DHQD)2PYR and from 100 to 300 mol % of NMO, always based on the amount of 3-phenyl cinnamate (II).

Suitable solvents used are mixtures of water with an organic solvent.

Particularly suitable mixtures have been found to be mixtures of water with alcohols, acetonitrile, and acetone in a ratio of from 0.1 to 5:1 w/w.

The reaction temperature is in the range of −20° C. to 100° C., temperatures below 75° C. being preferred.

In order to transform the diol to an epoxide, there are added to the diol from 1 to 10 equivalents of a base and from 1 to 3 equivalents of a sulfonyl chloride, an azodioic derivative, or a carbodiimide. In particular, preferred bases are tertiary amines, and sulfonyl chlorides are preferred for generation of a leaving group.

To introduce the leaving group in reaction step (b) use is preferably made of sulfonyl chlorides such as methanesulfonyl chloride and toluenesulfonyl chloride.

The reaction can be carried out as a one-pot process without isolation of an intermediate stage or as a two-stage process with isolation of the precursor of the epoxide. A preferred embodiment is the one-pot process.

Solvents for (b) or (c) are preferably aprotic solvents of medium polarity such as toluene or dichloromethane.

The reaction takes place at temperatures ranging from −70° C. to 100° C. Preference is given to reaction temperatures between −10° C. and 35° C.

The production of the corresponding 3-phenyl cinnamates (II) is known to the person skilled in the art from standard works of organic literature.

The conversion of 1,2-diols to epoxides is well-known and is described, for example, in the textbook by J. March, Advanced Organic Chemistry, 1985, Wiley, pages 270 and 345.

The invention also relates to the enantiomerically pure dihydroxy esters (III) obtained in the aforementioned process and forming valuable intermediate products for pharmaceutically active substances:

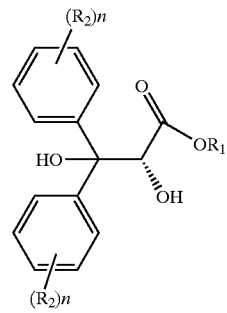

III in which $R_1$ denotes $C_1$–$C_{10}$ alkyl, aryl, or arylalkyl, particularly alkyl or benzyl, $R_2$ denotes $C_1$–$C_{10}$ alkyl, aryl, arylalkyl, halogen, $C_1$–$C_{10}$ alkoxy, acyloxy or amide, and n is 0 to 5, particularly 0.

The invention is illustrated below with reference to the following examples.

General Working Instructions

1.) Synthesis of 2,3-dihydroxy-3,3-diphenyl propionate a) AD-Mix Variant

In a flask there were placed 27.2 g of AD mix alpha, and 100 mL of water were added, 80 mL of 2-methylpropan-2-ol were added, and to this mixture there were added 5.6 g of tert-butyl 3-phenyl cinnamate dissolved in 20 mL of tert-butanol. The reaction was complete after 3 days at room temperature. To the two-phase system there were added 30 g of sodium sulfite dissolved in water and the mixture was stirred for half an hour. The organic phase was separated and the aqueous phase extracted with dichloromethane, and the combined organic phases were rewashed with water. The mixture was then dried over magnesium sulfate and the solvent removed by distillation. 4.8 g of a flocculent solid were isolated (HPLC purity 95%, the incorrect enantiomer was not considered).

b) N-methylmorpholine-N-oxide Variant (Slow Addition of Substrate):

In a flask there were placed 250 mg of $K_2OsO_2(OH)_4$, 750 mg of hydroquinidine-1,4-phthalazine-diy-ethyl ether and 30 mL of 50% strength N-methylmorpholine-N-oxide solution in 120 mL of tert-BuOH, and 90 mL of water, and the mixture was stirred until all was dissolved. 24 g of ethyl 3-phenylcinnamate were topped up with tert-butanol to a volume of 48 mL and passed directly into the solution at a rate of 1 mL/h. After ca 1 hour the solution changed color from violet to yellow, and after three hours solid matter began to precipitate. Following a period of 28 hours a solid paste had formed, and following a period of 50 hours a sodium sulfite solution was added thereto and the mixture was stirred for a period of 30 minutes. Dichloromethane and 1N HCl were then added, and the organic phase was separated and the solvent removed by distillation. The crude product was recrystallized from heptane and there were isolated 17 g of product as a white flocculate (98% purity, 61% yield).

c) N-methylmorpholine-N-oxide Variant (Direct Addition of Substrate)

In a flask there were placed 30 mg of $K_2OsO_2(OH)_4$, 95 mg the (DHQ)2PHAL and 4.2 mL of 50% strength N-methylmorpholine-N-oxide solution in 90 mL of isopropanol and 30 mL of water, and the mixture was stirred over a period of 2 hours. To the solution there were added 10 g of ethyl 3-phenylcinnamate, and the mixture was stirred for 48 hours at 0° C. Workup was effected by adding sodium sulfite solution and stirring over a period of 30 minutes. 50 mL of dichloromethane and 50 mL 1N HCl were then added, and the organic phase was separated and the solvent removed by distillation. The crude product was recrystallized from MTB/heptane and there were isolated 7 g of product as a white flocculate.

R-ethyl 2,3-dihydroxy-3,3-diphenylpropionate [alpha] 20=− 149 (methanol, c=1.589 nm).

2.) Formation of the glycide ester

Ethyl 2,3-dihydroxy-3,3-diphenylpropionate (12.4 g, 43 mmol) was used as initial batch in 260 mL of $CH_2Cl_2$ and, at 0° C., first triethylamine (17.5 g, 101 mmol) and then methanesulfonyl chloride (10 g, 86 mmol) were added. The solution was stirred over a period of 48 hours at room temperature. Workup was effected by washing the methylene chloride phase with 100 mL of 1N HCl and an $NaHCO_3$ solution. Following azeotropic distillation of residues of water with dichloromethane the glycide ester can be caused to react further in solution. In order to determine the yield, the solvent was removed by distillation and there were isolated 13 g of an oil, which had a purity of 94% as determined by HPLC.

What is claimed is:

1. A process for enantioselective production of glycide ester (I) by
   (a) dihydroxylation of a corresponding 3-phenyl cinnamate (II) by osmium (VIII) oxide catalysis in the presence of a Sharpless ligand and an oxidizing agent to form the dihydroxy ester (III),
   (b) selective conversion of the hydroxy function in the 2 position of the dihydroxy ester (III) to a leaving group,
   (c) intramolecular substitution of the leaving group through the hydroxy function in the 3 position to form the glycide ester (I),

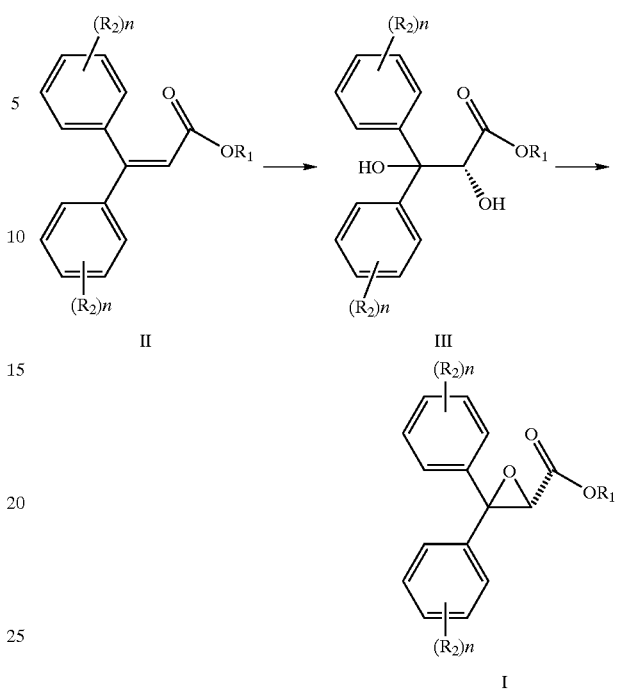

in which

R$_1$ denotes $C_1$–$C_{10}$ alkyl, aryl, or arylalkyl, which may be substituted, R$_2$ denotes $C_1$–$C_{10}$ alkyl, aryl, arylalkyl, halogen, $C_1$–$C_{10}$ alkoxy, acyloxy, or amide, which may be substituted, and n is 0 to 5.

2. A process as defined in claim 1, wherein the transformation of dihydroxy ester (III) to glycide ester (I) is carried out in a one-pot process without isolation of the intermediate stage.

3. A process as defined in claim 1, wherein the compound (III) used is a cinnamic derivative in which R$^1$ denotes alkyl or benzyl, and R$^2$ denotes H.

* * * * *